United States Patent [19]

Fink et al.

[11] Patent Number: 5,670,369
[45] Date of Patent: Sep. 23, 1997

[54] METHOD FOR THE PRODUCTION OF SOLUBLE COLLAGEN

[75] Inventors: David J. Fink, Shaker Hts.; Kevin M. Virnelson, Mayfield Hts., both of Ohio

[73] Assignee: Ranpak Corporation, Concord, Ohio

[21] Appl. No.: 670,338

[22] Filed: Jun. 25, 1996

[51] Int. Cl.$^6$ .............. C07K 1/00; C12P 21/06; A61K 38/17
[52] U.S. Cl. .......... 435/273; 435/68.1; 435/71.1; 435/184; 435/212; 435/213; 435/219; 435/265; 530/356
[58] Field of Search .................. 435/273, 68.1, 435/265, 71.1, 184, 212, 213, 219; 530/356

[56] References Cited

U.S. PATENT DOCUMENTS

| | | | |
|---|---|---|---|
| 3,034,852 | 5/1962 | Nishikara | 264/202 |
| 3,314,861 | 4/1967 | Fujii | 435/68.1 |
| 3,532,593 | 10/1970 | Young | 162/2 |
| 3,616,205 | 10/1971 | Ito | 435/273 |
| 4,066,083 | 1/1978 | Rics | 424/400 |
| 4,140,537 | 2/1979 | Luck et al. | 106/160.1 |
| 4,233,360 | 11/1980 | Luck et al. | 424/443 |
| 4,293,647 | 10/1981 | Monsheimer et al. | 435/68.1 |
| 4,488,911 | 12/1984 | Luck et al. | 106/157.2 |
| 4,655,980 | 4/1987 | Chu | 264/102 |
| 5,316,942 | 5/1994 | Fink | 435/273 |
| 5,460,967 | 10/1995 | Fink | 435/273 |

FOREIGN PATENT DOCUMENTS

| | | |
|---|---|---|
| 1145904 | 6/1961 | Germany . |
| 1062083 | 3/1967 | United Kingdom . |

OTHER PUBLICATIONS

"Science and Technology of Gelatin", A.G. Ward and A. Courts, Academic Press, 1977, pp. 152–153 and 165–166.
Tkac, J. et al., "The Use of Collagen Dispersions During the Manufacture of Paper," Kozarstvi 30; 11; pp. 324–326.

*Primary Examiner*—John W. Rollins
*Assistant Examiner*—Christopher R. Tate
*Attorney, Agent, or Firm*—Renner, Otto, Boisselle & Sklar

[57] ABSTRACT

The invention includes an improved method for producing an aqueous solution of soluble collagen. The method comprises the steps of:

(A) providing an aqueous ground slurry of insoluble collagen containing insoluble collagen at a first concentration and at a pH effective to obtain activity for a proteolytic enzyme added in step (B);

(B) adding a proteolytic enzyme to said slurry;

(C) reacting said slurry and enzyme at a temperature, $T_1$, and for a time $t_1$ effective for forming a slurry containing at least some soluble collagen;

(D) diluting at least a portion of the slurry formed in step (C) with water to form a diluted slurry containing insoluble collagen at a second concentration; and (E) reacting said diluted slurry obtained in step (D) at a temperature, $T_2$ and for a time $t_2$, effective to produce a solution containing an increased amount of soluble collagen.

The improved process of the present invention permits the preparation of soluble collagen utilizing reduced amounts of enzyme and water, and requires less time at low concentration for completion of the reaction.

29 Claims, 2 Drawing Sheets

METHOD FOR THE PRODUCTION OF SOLUBLE COLLAGEN

FIELD OF THE INVENTION

This invention relates to an improved method for the production of soluble collagen, and more particularly, to an enzymatic method of producing soluble collagen which utilizes a reduced amount of water, enzyme and time to complete the reaction.

BACKGROUND OF THE INVENTION

Skin is composed of four distinct layers, which are, proceeding from outside-in: (1) a thin outer layer of epithelium termed the "epidermis," which is rich in the protein keratin, not collagen; (2) a dense collagen-rich layer, termed the "dermal" or "grain" layer, also called in the older literature the "thermostat" layer; (3) a thicker layer of less-dense, collagen-rich connective tissues, termed the "corium" layer; and (4) an inner layer of "subcutaneous tissue," known to the tanner as "flesh," by which the skin is attached to the underlying tissue.

Although hides may merely be "cured" in salt and/or other biocidal solutions to stop microbial degradation, many hides that are intended for use in leather manufacture are "limed," that is, soaked in a saturated solution of hydrated lime (calcium hydroxide) and water. The liming process initiates the loosening of the epidermis and the subcutaneous layer, and is the first step in the dehairing process. After liming is complete, the hair, epidermis, and any residual flesh, fat and surface muscles are removed by mechanical scraping, and the dermal layer is mechanically cut, along with enough of the corium layer to give the final leather its required thickness, from the remaining inner corium layer.

In leather-making the primary interest is on the dense collagen-rich dermal layer, which is about 25% of the thickness of the corium layer. During the process of leather-making, the dermal tissue receives separate chemical and tanning treatments to stabilize the collagen structure.

The residual portion of the corium layer that is separated from the dermal layer is termed the "limed split" and is a by-product waste of the leather manufacturing process. It is these limed splits that become, for example, the collagen-rich feedstock for sausage casing production, and that have been used as the source of collagen for the examples herein.

During the liming process, the skin imbibes and binds water, and becomes highly swollen; in the process it acquires a very alkaline pH of about 12.5. The chemistry of the liming process is quite well understood. Prior to further leather processing, and in the collagen production process considered here, the skins must be "delimed" by soaking in acid or salt solutions.

The decomposition of skins and the like with the aid of proteolytic enzymes has been described in the prior art. U.S. Pat. Nos. 4,140,537; 4,233,360; 4,488,911; and 4,655,980, all assigned to Collagen Corporation, describe enzymatic methods, including pepsin hydrolysis for solubilizing collagen to produce a "non-immunogenic" soluble collagen which is then converted to other forms for use as medical implants.

U.S. Pat. No. 3,616,205 (Ito) describes a method for solubilizing insoluble collagen which comprises treating said insoluble collagen at a temperature of from 0° to about 37° C. at a pH of 1.5 to 3.0 with a collagen solubilizing proteolytic enzyme. The enzyme treatment and the acid extraction of the collagen are effected simultaneously. U.S. Pat. No. 4,293,647 discloses a method for dissolving collagen-containing tissues such as wastes arising in leather processing. The process comprises enzymatically hydrolyzing said tissues with at least one acid protease at a pH within the acid region. The liquid hydrolyzates so obtained can thereafter be biologically decomposed. GB Patent 1,062,0.83 describes a method for solubilizing insoluble collagen into a fiber reconstitutable form in an aqueous solution. The method comprises treating said collagen with a proteolytic enzyme other than collagenase, which enzyme is active in a pH range of 2 to 10 in the presence of an aqueous solution of a cationic surfactant and/or at least one water-soluble divalent metal salt of calcium, magnesium, barium, strontium, zinc, cadmium or manganese with hydrochloric, sulfuric, thiosulfuric or acetic acid. Treatment can be carried out at a pH between 2 and 10 and at a temperature below the denaturing temperature of collagen. U.S. Pat. No. 3,034,852 and related German Patent 1,145,904 (Nishihara) also describe the method for improving the production of collagen or collagen solutions. The method involves subjecting the collagen-containing material to a preliminary treatment in an enzyme solution at a temperature lower than 60° C. (or below 45° C.) and extracting the collagen with a dilute and (pH about 1–4) hereby a collagen solution: is produced.

The use of proteolytic enzymes to facilitate the acid-solubilization of insoluble collagen also is described in "*The Science and Technology of Gelatin*", A. G. Ward and A. Courts, *Academic Press*, 1977 (pp. 152-3 and 165–6). The preparation of collagen dispersions using enzymes is described by Tkac, J. et al in "*The Use of Collagen Dispersions During the Manufacture of Paper,*" Kozarstvi 30; 11; 1980; pp. 324–26.

Enzymatic processes for preparing soluble collagen also have been described recently in U.S. Pat. Nos. 5,316,942 (Fink) and 5,460,967 (Fink and Brody). The process described in U.S. Pat. No. 5,316,942 generally comprises the steps of (a) providing an aqueous ground slurry of insoluble collagen; (b) adjusting the water or solid content of the slurry whereby the insoluble collagen is at a concentration that promotes substantially maximum solubilized collagen concentration and molecular weight in the final product; (c) adjusting the pH of the slurry to obtain activity for a proteolytic enzyme; (d) adding a proteolytic enzyme to the pH adjusted slurry and reacting at a temperature for a time effective to form high molecular weight solubilized collagen; (e) controlling the reaction conditions to obtain a high concentration of soluble collagen and a high molecular weight of the solubilized collagen by simultaneously measuring the concentration of solubilized collagen and the molecular weight of the solubilized collagen; (f) adding additional water and insoluble collagen to the solution; and (g) separating at least some of the solution containing high molecular weight solubilized collagen from the insoluble collagen and returning the insoluble collagen to step (b) whereby at least a portion of the proteolytic enzyme is recycled. The separated solution containing high molecular weight solubilized collagen is withdrawn as a product. A similar procedure is described in U.S. Pat. No. 5,460,967 which does not require recycling of a portion of the proteolytic enzyme.

The present invention provides a lower cost method of preparing soluble collagen enzymatically.

SUMMARY OF THE INVENTION

An improved method for producing an aqueous solution of soluble collagen from insoluble collagen is described. The method comprises the steps of:

(A) providing an aqueous ground slurry of insoluble collagen containing insoluble collagen at a first concentration and at a pH effective to obtain activity for a proteolytic enzyme added in step (B);

(B) adding a proteolytic enzyme to said slurry;

(C) reacting said slurry and enzyme at a temperature, $T_1$ and for a time $t_1$ effective for forming a slurry containing at least some soluble collagen;

(D) diluting at least a portion of the slurry formed in step (C) with water to form a diluted slurry containing insoluble collagen at a second concentration; and (E) reacting said diluted slurry obtained in step (D) at a temperature, $T_2$ and for a time $t_2$ effective to produce a solution containing an increased amount of soluble collagen. The improved process of the present invention permits the preparation of soluble collagen utilizing reduced amounts of enzyme and water, and requires less time at low concentration for completion of the reaction.

DETAILED DESCRIPTION OF THE INVENTION

Figure 1:
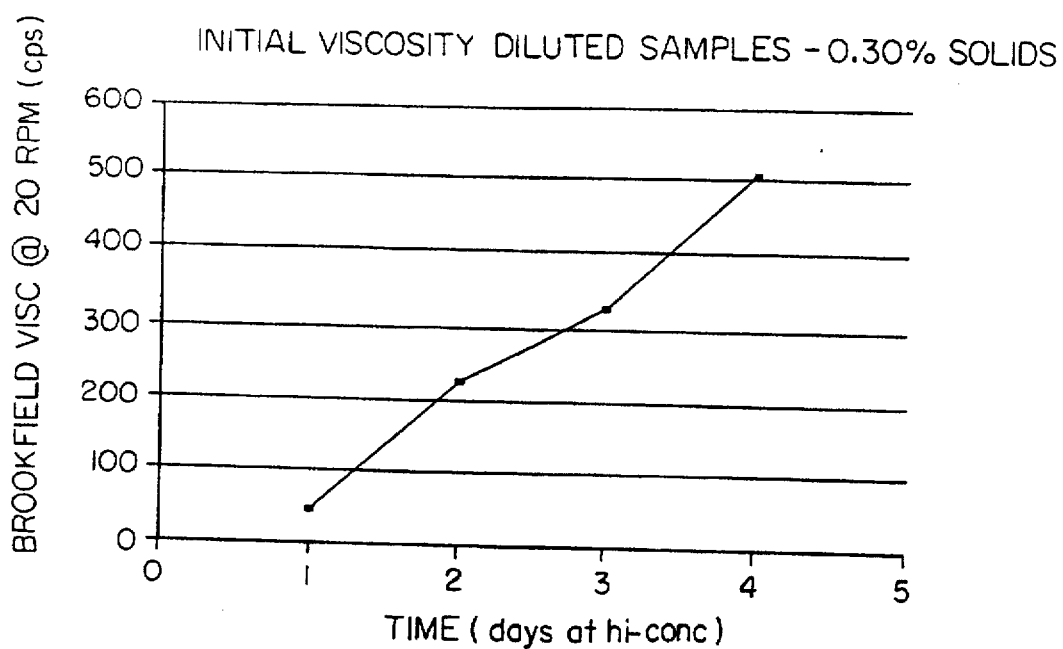
FIG. 1 is a plot of the initial viscosity of four samples of high concentration mixture of Example 1 at 20 rpm taken after each of four days and diluted with water.

Throughout the specification and claims, and unless otherwise indicated, the term soluble collagen is defined as collagen that has been treated to separate the collagen fibrils to render them soluble in water while retaining the normal triple-helical assembly of native collagen. Covalent bonds between the collagen fibrils are broken forming smaller collagen molecules which are soluble in water.

The process of the present invention can be generally characterized as occurring in two stages: a first concentration stage (high concentration) followed by a second concentration stage (lower concentration). The two-stage process of the present invention provides soluble collagen having desirable properties in less time at low concentration than required when the entire reaction is conducted in a dilute aqueous slurry of insoluble collagen (i.e., 0.1% to 1% solids) such as in the methods described in U.S. Pat. Nos. 5,316,942 and 5,460,967. The two-stage process of the present invention also can be conducted with reduced enzyme levels.

The improved process of the present invention for producing an aqueous solution of soluble collagen comprises the steps of:

(A) providing an aqueous ground slurry of insoluble collagen at a first concentration and at a pH effective to obtain activity for a proteolytic enzyme added in step (B);

(B) adding a proteolytic enzyme to said slurry;

(C) reacting said slurry and enzyme at a temperature, $T_1$ and for a time $t_1$ effective for forming a slurry containing at least some soluble collagen;

(D) diluting at least a portion of the slurry formed in step (C) with water to form a diluted slurry containing insoluble collagen at a second concentration; and (E) reacting said diluted slurry obtained in step (D) at a temperature, $T_2$ and for a time $t_2$ effective to produce a solution containing an increased amount of soluble collagen. The first concentration or insoluble collagen generally is in the range of about 1.2% to about 5% by weight. The second concentration of insoluble collagen is lower than the first concentration and is generally in the range of about 0.1% to about 1% by weight.

In a preferred embodiment, the process of this invention comprises the steps of (A) providing an aqueous ground slurry of insoluble collagen containing from about 1.2% to about 5.0% by weight of insoluble collagen at a pH effective to obtain activity for a proteolytic enzyme added in step (B);

(B) adding a proteolytic enzyme to said slurry;

(C) reacting said slurry and enzyme at a temperature, $T_1$ and for a time $t_1$ effective for forming a slurry containing at least some soluble collagen;

(D) diluting at least a portion of the slurry formed in step (C) with water to form a diluted slurry containing from about 0.1% to about 1% by weight of insoluble collagen; and (E) reacting said diluted slurry obtained in step (D) at a temperature, $T_2$ and for a time $t_2$ effective to produce a solution containing an increased amount of soluble collagen. Steps (A) thru (C) comprise the first stage, and steps (D) and (E) comprise the second stage of the improved method.

In the procedures described in U.S. Pat. Nos. 5,316,942 and 5,460,967, the concentration of insoluble collagen in the initial slurries is indicated as being from about 0.1% to 1% by weight. In the examples, concentrations of insoluble collagen of about 0.31% to 0.34% by weight are prepared and reacted with the enzyme. Accordingly, one difference in the process of the present invention from the process of the '942 and '967 patents is that there is an initial reaction between the insoluble collagen at a higher solids concentration (about 1.2% to 5%) and thereafter, the reaction is completed at a dilute concentration similar to the concentrations used in the '942 and '967 patents. When the solubilization reaction is initiated at the higher concentrations of the present invention, a significantly reduced amount of water and space for the vessels containing the slurry are required. When the partially reacted or solubilized mixture subsequently is diluted for completion of the reaction, the solubilization of the insoluble collagen in the diluted slurry proceeds more rapidly than when the entire solubilization reaction is conducted at the same dilution.

In the first step of applicants' process, a relatively concentrated aqueous ground slurry of insoluble collagen is prepared containing from about 1.2% to about 5.0% by weight of insoluble collagen. In one preferred embodiment, the concentration is from about 2.0% to about 3.5% by weight and in a further embodiment, the concentration is from about 3.0% to about 3.5% by weight. The pH of the aqueous slurry of insoluble collagen is adjusted to obtain activity for a proteolytic enzyme which is added in a subsequent step. Typically, the pH of the relatively concentrated aqueous slurry of insoluble collagen is dependent upon the particular enzyme utilized in the slurry, but generally, the aqueous slurry of insoluble collagen is adjusted to provide an acidic pH of between about 1 and about 6 and more often between about 1.5 and about 2.5 or even 3.0. The desired pH of the slurry can be established by the addition of suitable acids, acid salts, buffers, etc., which are not harmful to the enzyme. For example, hydrochloric acid, sulfuric acid, phosphoric acid, acetic acid and citric acid, or the acid salts of sulfuric and phosphoric acids can be used as acids.

A proteolytic enzyme is added to the aqueous ground slurry which is effective in promoting the conversion of the insoluble collagen to soluble collagen. The amount of enzyme utilized in the method of the present invention may be varied over a wide range. Generally, the use of a large amount of enzyme is unnecessary and is avoided because of the added expense. Those familiar with this art will recognize that the optimum ratio of enzyme-containing solids to collagen-containing solids will depend on the type of enzyme used and the specific activity of each enzyme preparation. In one embodiment, the amount of enzyme included in the relatively concentrated aqueous ground slurry of insoluble collagen may range from about 0.01 gram to about 0.25 gram of crude enzyme preparation per gram of collagen solids contained in the aqueous slurry. Alternatively, the concentration of crude enzyme preparation may range from about 1% to about 25% by weight based on the initial weight of insoluble collagen in the aqueous slurry.

After the proteolytic enzyme has been added to the relatively concentrated aqueous ground slurry of insoluble collagen, the enzyme is reacted with the insoluble collagen at a temperature ($T_1$) and for a time $t_1$ effective for forming a slurry containing at least some soluble collagen. Generally, the aqueous slurry and enzyme mixture is maintained at a temperature ($T_1$) of from about 5° C. up to but not including the denaturing temperature of the collagen. In a preferred embodiment, the temperature ($T_1$) may range from about 5° C. to about 35° C., and in a more preferred embodiment, the temperature ($T_1$) is from about 15° C. to about 25° C. At the lower temperatures, the reaction generally is slower than at the higher temperatures. An ideal temperature appears to be in the range of 19° C. to 22° C. The reaction between the enzyme and the insoluble collagen in the high concentration slurry is conducted for a period of time ($t_1$) sufficient to form the desired amount of soluble collagen in the concentrated mixture. The time ($t_1$) required to form the desired amount of soluble collagen in the concentrated slurry (and in the diluted slurry) is dependent on several factors including the type, source and processing of the insoluble collagen, the pH and temperature of the diluted slurry, and the enzyme concentration employed. Thus the time ($t_1$) can be readily determined by experimentation.

The insoluble collagen utilized in the process of the present invention may be derived from a variety of sources so long as the feed is relatively clean and contains collagen-containing material of relatively small particle size. Particularly useful sources of insoluble collagen are the collagen-containing waste materials from leather preparation such as skin scraps, limed splits, machine fleshings, etc., obtained from animal hides such as steer hides and cow hides.

One method for providing the aqueous ground slurry of insoluble collagen utilized in the method of the present invention includes the steps of: (a) providing soft animal tissues containing collagen; (b) cleaning the collagen-containing tissues to remove hair, fat, carbohydrates and other contaminants; (c) cutting the cleaned collagen-containing tissues into small pieces; (d) mixing the small pieces with water to obtain a slurry; (e) wet-grinding the resulting slurry to obtain a slurry of insoluble collagen. The pH of the slurry of this method is typically from about 3 to about 7. Depending on the source and pretreatment of the animal hides used, the hides may need to be delimed or acidified to remove residual calcium salts or other biocides since the presence of such chemicals can delay or hinder the reaction between the enzyme and the insoluble collagen. The time ($t_1$) required for forming the desired amount of soluble collagen can be readily determined by one skilled in the art by experimentation with a particular source of insoluble collagen.

The proteolytic enzymes utilized in the present invention are those which are effective on the insoluble collagen. Many different sources of collagen can be used, and it is not possible to enumerate all of the proteolytic enzymes that can be used with the process of the invention. However, the proteolytic enzyme which is effective for a particular source of soluble collagen can be readily determined by one skilled in the art. Some examples of proteolytic enzymes useful in the method of the present invention include those selected from the group consisting of porcine mucosal pepsin, bromelain, chymopapain, chymotrypsin, collagenase, ficin, papain, peptidase, proteinase A, proteinase K, trypsin, microbial proteases, and, similar enzymes or combinations of such enzymes. Typically, these enzymes are active at a pH of between 1 and about 5, and more often from about 1.5 to about 3.0.

Generally, the enzyme and insoluble collagen in the concen- trated slurry are allowed to react for a period of from about 6 hours up to about 20 or 24 days or longer. More often, the reaction between the enzyme and the insoluble collagen in the concentrated slurry is allowed to proceed for about 12 hours to about 20 days. A reaction time of from about 12 hours to about 1 day or even up to about 6 days is generally sufficient to provide a concentrated slurry containing a desired amount of soluble collagen. The reaction can be temporarily stopped by lowering the temperature of the concentrated slurry to about 0° to 10° C. When the temperature is raised, the reaction continues.

In the second stage of the method of the present invention, the at least partially reacted concentrated slurry containing at least some soluble collagen is diluted with water to form a diluted slurry containing from about 0.1 to about 1% by weight of insoluble collagen. The insoluble collagen contained in this diluted slurry is then allowed to react with the enzyme present in the diluted slurry at a temperature ($T_2$) and for a time ($t_2$) effective to produce a solution containing an increased amount of soluble collagen. In one preferred embodiment, the concentrated slurry is diluted with sufficient water to provide a diluted slurry containing from about 0.20% to about 0.40% by weight of insoluble collagen and substantially all of the insoluble collagen is converted to soluble collagen. The pH of the diluted slurry should be adjusted, if necessary, to a pH of about 1.5 to about 3.0. An average pH of about 2 is desirable. The temperature of the reaction between the insoluble collagen in the diluted slurry and the enzyme is generally between about 5° C. up to but not including the denaturing temperature of the collagen. Temperatures of from about 5° C. up to about 35° C. are preferable, and temperatures of between about 15° C. to about 25° C. are more preferable. The enzyme is reacted with the insoluble collagen in the dilute slurry for a period of time which is sufficient to produce a solution containing the desired amount of soluble collagen. The time ($t_2$) required to produce the desired amount of soluble collagen is determined in part by the temperature of the reaction (reaction rate is proportional to reaction temperature) and on the source and type of insoluble collagen used in the formation of the aqueous slurry. For example, the collagen containing wastes from leather preparations may contain chemicals which delay or hinder the enzymatic reaction. Generally, however, reaction times of from about 6 to about 30 or 40 hours are sufficient.

In one preferred embodiment, the reaction between the insoluble collagen in diluted slurry and the enzyme is monitored and controlled to obtain a solution having a high concentration of soluble collagen. The progression of reaction can be monitored either (a) directly, by measurement of the concentration and/or molecular weight distribution of resulting soluble molecules, or (b) indirectly, by measuring a functional property that can be correlated with the soluble concentration or molecular weight distribution. In one embodiment, the soluble collagen concentration is measured by centrifugation of the reaction mixture to remove undissolved solids, followed by quantification of collagen concentration in the soluble fraction by methods measuring hydroxyproline content. Methods for determining molecular weight distribution include High Performance Liquid Chromatography (HPLC), Gel Permeation Chromatography (GPC), and PolyAcrylamide Gel Electrophoresis (PAGE). In one embodiment, the reaction can be monitored by measuring the concentration and number average molecular weight of the soluble collagen whereby the reaction is considered complete when the $\overline{Mn}$ is at least about 300,000 daltons and the concentration of the soluble collagen is maximized. The reaction between the insoluble collagen in the diluted slurry and the enzyme may be terminated by inactivating the proteolytic enzyme (e.g., raising the pH of the diluted slurry) and/or reducing the temperature of the diluted slurry.

The progress of the reaction between the enzyme and the insoluble collagen typically can be followed or monitored by periodic measurement of the viscosity of the solution as the solution is being formed. The viscosity of the solution increases as the concentration of high molecular weight soluble collagen increases. Fluid viscosities of the solutions can be conveniently measured by a variety of relatively simple methods utilizing apparatus such as the model LVF Brookfield viscometer, spindles numbers 2 or 3. Alternatively, viscosity readings can be measured on a Brookfield model RVF viscometer using spindle number 3. The reaction can be considered to be complete when the viscosity of the solution begins to level off after time.

The progress of the reaction also can be monitored by periodically measuring the solution viscosity at two different shear rates whereby the reaction is considered complete when the ratio of (the viscosity at low shear) to (the viscosity at high shear) is substantially maximized. The viscosity ratio is preferably at least 75% of maximum. In another embodiment, at least about 80% by weight of the insoluble collagen is converted to soluble collagen at the end of the second stage.

The soluble collagen prepared by the process of the invention retains the normal triple-helical assembly of native collagen. Thus, the soluble collagen is characterized as having a relatively high number average molecular weight. In one embodiment, the number average molecular weight ($\overline{Mn}$) of the soluble collagen is above 300,000 daltons and is more preferably above 600,000 daltons. In a most preferred embodiment, at least 90% by weight of the insoluble collagen is converted to soluble collagen, and the $\overline{Mn}$ of the soluble collagen is above 1,000,000 daltons.

The process of the present invention results in the production of an aqueous solution of soluble collagen in high yield while reducing the time at low concentration, enzyme level and the amount of water required for most of the solubilization reaction to occur. The process can be and usually is conducted in the absence of added urea, water-soluble divalent metal salts of calcium, magnesium, barium, strontium, zinc, cadmium, or manganese with hydrochloric acid, sulfuric acid, thiosulfuric acid or acetic acid, and/or cationic surfactants. The amount of tankage required for solubilization is significantly reduced because the initial steps of the process (first stage) are conducted utilizing a concentrated aqueous ground slurry of the insoluble collagen. It has been observed that when utilizing the present process, the amount of proteolytic enzyme added to the aqueous ground slurry also can be reduced while still producing the desired amount and type of soluble collagen.

Those familiar with the industrial sites in which large-scale uses of soluble collagen might be conducted will recognize that a reduction of on-site tankage for the preparation of soluble collagen will result in significantly improved use of the collagen product. The two-stage process leading to the production of soluble collagen permits the physical separation of the first and second stages. Therefore, preparation of the insoluble collagen feedstock and the preliminary solubilization process (stage 1) could be conducted, for example, at a centralized processing facility. The reaction can be interrupted by lowering the temperature of the slurry. Following transportation of the concentrated slurry at a lower temperature to the site of use, final solubilization of the product (stage 2) can then be conducted with the requirement of less tankage than if both stages were conducted at the site of use. It is to be recognized also that some of the preliminary solubilization reaction may also occur during the transportation of the slurry between the two sites.

The following examples illustrate the method of the present invention for preparing soluble collagen from insoluble collagen. Unless otherwise indicated in the following examples and elsewhere in the specification and claims, all parts and percentages are by weight, temperatures are in degrees Centigrade, and pressure is at or near atmospheric pressure. The source of insoluble collagen in the examples is limed splits purchased from Seton Company, Newark, N.J., U.S.A. The splits are ground into small pieces following the methods described by Turkot, Komanowsky and Sinnamon in Food Technology, April, 1978, pp. 48–57, except that the splits are not neutralized prior to the cutting and grinding steps. Small pieces of insoluble collagen are prepared by passing the collagen through an Urschel Laboratories Comitrol comminuting machine, Model No. 1700 with an 0.06" cutting head. These pieces are mixed with water to form the slurry. Animal stomach enzyme (pepsin) is used in each of the examples, and was purchased from Sigma Chemical Company, St. Louis, Mo., as a crude preparation, Catalog No. P-7125, Lot 45HO867. This pepsin preparation contained approximately 15% protein (by UV) with an activity of 140 pepsin units/mg and 920 units/mg protein.

EXAMPLE 1

A high concentration collagen solids slurry (2.5% solids) is prepared in water, and the pH of the mixture is adjusted with hydrochloric acid to 1.98. Pepsin powder (0.11 gram pepsin/gram collagen solids) is added to the collagen slurry with stirring to initiate the reaction. This concentrated slurry is maintained at 19° C. for four days. A sample (Day 1 Sample) of the concentrated slurry is taken after one day and diluted with water to a concentration of 0.30% by weight solids. The pH of the diluted mixture is adjusted to and maintained at about 2.1, and the temperature of the diluted slurry is maintained at between 18° C. and 21 ° C. The rate and degree of reaction between the pepsin and the insoluble collagen in the diluted slurry is monitored by measuring the viscosity of the diluted solution at 20 rpm and 100 rpm immediately upon formation and periodically thereafter utilizing a Brookfield model RVF Viscometer (Spindle No. 3).

Samples of the high concentration slurry also are taken after two (Day 2 Sample), three (Day 3 Sample), and four (Day 4 Sample) days and each of the samples is diluted with water to 0.30% solids. The pH of these samples is adjusted to about 2.1 and the diluted slurry is maintained at about 18–21 ° C. The viscosities of the diluted mixture are determined at the initial time of dilution of each sample and periodically thereafter.

A control sample also is prepared directly as a dilute aqueous slurry of the same ground lime splits (0.30% solids) and the mixture is adjusted to a pH of 2.1 with concentrated hydrochloric acid. Pepsin (0.11 gram of pepsin/gram collagen solids) is added to the diluted slurry with stirring to initiate the reaction, and the slurry is maintained at a temperature of from about 18° C. to 21 ° C. The viscosity of this control solution is determined initially upon formation and periodically thereafter.

Figure 2:
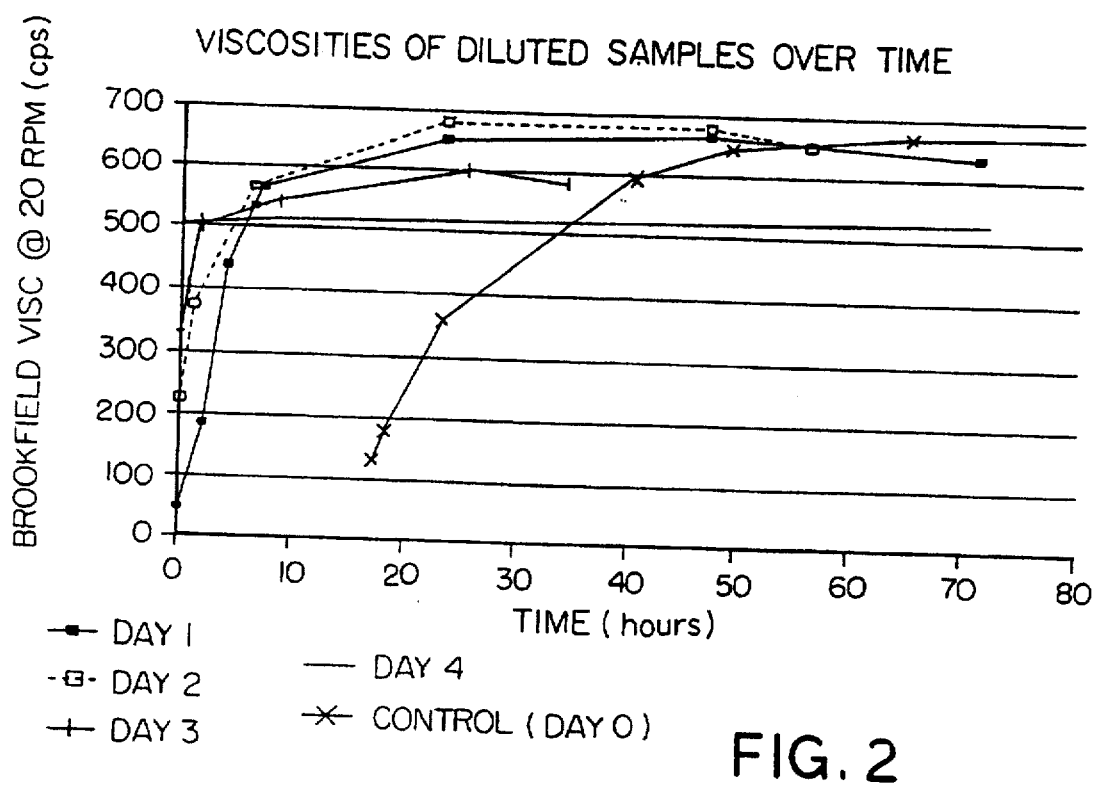
FIG. 2 is a plot of the viscosities over time of the four samples taken from the high concentration mixture of Example 1 and diluted, and these viscosities are compared to a control sample.

The results of the viscosity determinations of the various samples are reported in Tables I–V, and illustrated in FIGS. 1 and 2.

TABLE I

Day 1 Sample

| Time (hours) | Visc. @ 20 rpm | Visc. Ratio |
| --- | --- | --- |
| 0 | 45 | 1.02 |
| 2 | 185 | 2.06 |
| 4 | 440 | 2.40 |
| 6 | 535 | 2.62 |
| 7 | 585 | 2.62 |
| 23 | 650 | 2.66 |
| 47 | 665 | 2.61 |
| 71 | 635 | 2.61 |

TABLE II

Day 2 Sample

| Time (hours) | Visc. @ 20 rpm | Visc. Ratio |
| --- | --- | --- |
| 0 | 225 | 2.21 |
| 1 | 375 | 2.23 |
| 6 | 565 | 2.59 |
| 23 | 680 | 2.59 |
| 47 | 680 | 2.64 |
| 58 | 650 | 2.59 |

TABLE III

Day 3 Sample

| Time (hours) | Visc. @ 20 rpm | Visc. Ratio |
| --- | --- | --- |
| 0 | 325 | 2.23 |
| 0.5 | 405 | 2.24 |
| 1.5 | 495 | 2.51 |
| 8.5 | 545 | 2.66 |
| 25 | 605 | 2.65 |
| 34 | 585 | 2.66 |

TABLE IV

Day 4 Sample

| Time (hours) | Visc. @ 20 rpm | Visc. Ratio |
| --- | --- | --- |
| 0 | 505 | 2.54 |
| 2.7 | 510 | 2.71 |
| 4 | 510 | 2.54 |
| 7 | 515 | 2.65 |
| 7.5 | 515 | 2.70 |
| 72 | 530 | 2.60 |

TABLE V

Control Sample

| Time (hours) | Visc. @ 20 rpm | Visc. Ratio |
| --- | --- | --- |
| 17 | 135 | 1.73 |
| 18 | 180 | 2.02 |
| 23 | 360 | 2.17 |
| 40 | 595 | 2.38 |
| 49 | 595 | 2.38 |
| 66 | 670 | 2.48 |
| 137 | 685 | 2.67 |

FIG. 1 is a plot of the initial viscosity at 20 rpm of the four samples (Day 1 thru Day 4 Samples) immediately upon dilution.

FIG. 2 is a plot of the viscosities of the four samples (Day 1 thru Day 4) initially and over a period of time. FIG. 2 also contains a plot of the viscosities of the control sample initially and over time.

As can be seen from the viscosities reported in the above tables and in the figures, the viscosity of the four day samples and the control sample all increased over time, but when the process of the present invention is utilized, (Day 1 thru Day 4 samples) the peak viscosity at 20 rpm is reached in a shorter period of time when compared to the control sample which was not subjected to an initial high concentration reaction. For example, the Day 1 sample reaches peak viscosity (665 cps) in 47 hours after dilution, Day 2 sample reaches its maximum viscosity after 23 hours, and Day 3 sample reaches its maximum viscosity after 25 hours. In contrast, the Control sample reached its maximum viscosity between 65 and 137 hours.

For the purpose of illustrating the benefits of the two-stage process of this invention, therefore, assume that the control reaction (1-stage, low concentration process at 0.3% total solids) is completed in 72 hours, while the two-stage process can be completed with the same enzyme usage by reacting for 48 hours at 2.5% solids and then 24 hours at 0.3% solids. If the batch reaction is conducted in a tank of suitable size to achieve the daily usage rate of the soluble collagen, the 1-stage process would require 3-tank days to complete the reaction, while the 2-stage would require only 1.24 tank-days to achieve the same effect. This difference represents an approximately 59% savings in tankage resulting from the 2-stage process.

EXAMPLE 2

Three high-concentration solutions (2.50% collagen solids) are prepared, and after the pH is adjusted to about 2.1, pepsin is added with stirring to each of the three samples at the following levels: 0.025 gram pepsin/gram collagen solids; 0.050 gram pepsin/gram collagen solids; and 0.100 gram pepsin/gram collagen solids, respectively. Samples of each of the three concentrated slurry are taken after one day, two days, and three days, and immediately diluted with water to a solids concentration of 0.30% by weight. The pH of each of the samples is adjusted to about 2.1, and the dilute slurry is maintained at a temperature in the range of about 18–22° C. The viscosity of each of the samples is measured initially and periodically thereafter. The results of the viscosity measurements on the samples are summarized in the following Tables VI–IX.

TABLE VI

| | Day 1 Sample | | | | | |
|---|---|---|---|---|---|---|
| | 0.025 g/g | | 0.050 g/g | | 0.100 g/g | |
| Time (hours) | 20 rpm | Visc. Ratio | 20 rpm | Visc. Ratio | 20 rpm | Visc. Ratio |
| 0 | 10 | 0.63 | 10 | 0.53 | 15 | 0.60 |
| 2 | 25 | 0.61 | 35 | 0.83 | 180 | 2.09 |
| 6 | 95 | 1.44 | 170 | 2.10 | 475 | 2.58 |
| 21 | 775 | 2.46 | 775 | 2.78 | 525 | 2.65 |
| 26 | 890 | 2.57 | 850 | 2.79 | 585 | 2.72 |
| 30 | 915 | 2.59 | 850 | 2.80 | 595 | 2.70 |
| 45 | 980 | 2.83 | 905 | 2.87 | 620 | 2.71 |

TABLE VII

| | Day 2 Sample | | | | | |
|---|---|---|---|---|---|---|
| | 0.025 g/g | | 0.050 g/g | | 0.100 g/g | |
| Time (hours) | 20 rpm | Visc. Ratio | 20 rpm | Visc. Ratio | 20 rpm | Visc. Ratio |
| 0 | 55 | 1.17 | 130 | 1.67 | 375 | 2.45 |
| 2 | 110 | 1.87 | 255 | 2.34 | 550 | 2.64 |
| 4 | 205 | 2.28 | 435 | 2.42 | 575 | 2.73 |
| 6.5 | 385 | 2.08 | 500 | 2.35 | 625 | 2.62 |
| 7.5 | 410 | 2.10 | 520 | 2.45 | 645 | 2.77 |
| 23 | 570 | 2.23 | 595 | 2.46 | 700 | 2.75 |
| 32 | 575 | 2.19 | 580 | 2.52 | 665 | 2.74 |

TABLE VIII

| | Day 3 Sample | | | | | |
|---|---|---|---|---|---|---|
| | 0.025 g/g | | 0.050 g/g | | 0.100 g/g | |
| Time (hours) | 20 rpm | Visc. Ratio | 20 rpm | Visc. Ratio | 20 rpm | Visc. Ratio |
| 0 | 110 | 1.55 | 220 | 2.18 | 440 | 2.33 |
| 1.5 | 170 | 1.95 | 400 | 2.33 | 450 | 2.57 |
| 4.5 | 350 | 2.30 | 510 | 2.58 | 455 | 2.50 |
| 7.5 | 440 | 2.27 | 590 | 2.68 | 470 | 2.58 |

TABLE IX

| | Control Sample | | | | | |
|---|---|---|---|---|---|---|
| | 0.025 g/g | | 0.100 g/g | | 0.100 g/g | |
| Time (hours) | 20 rpm | Visc. Ratio | 20 rpm | Visc. Ratio | 20 rpm | Visc. Ratio |
| 19 | 325 | 2.37 | 305 | 2.48 | 425 | 2.31 |
| 25 | 625 | 2.55 | 700 | 2.58 | 575 | 2.33 |
| 40 | 755 | 2.61 | 815 | 2.53 | 745 | 2.37 |
| 45 | 720 | 2.54 | 775 | 2.54 | 775 | 2.38 |

The results which are summarized in Tables VI–IX demonstrate that digesting the ground limed splits for one or a few days at high concentration (2.5% by weight) reduces the time to finish the reaction at low concentration. The peak viscosities after three and four days of high concentration digestion is generally less than the peak viscosity for the Day 1 and Day 2 samples and the Control. In the high concentration slurries, it is possible that the enzyme converts the collagen to a lower molecular weight soluble collagen causing it to be less viscous. However, when the entire reaction is conducted at lower concentrations (about 0.30% solids), higher peak viscosities may be obtained, but the reaction takes significantly more time and water.

For the purpose of illustrating the benefits of the two-stage process of this example, therefore, assume in this example that the control reaction (1-stage, low concentration process at 0.3% total solids and 0.10 g enzyme/g collagen) is completed in 48 hours, while the 2-stage process can be completed at lower enzyme usage by reacting for 48 hours at 2.5% solids and 0.025 g/g, followed by 24 hours at 0.3% solids. If the batch reaction is conducted in a tank of suitable size to achieve the daily usage rate of the soluble collagen, then the 1-stage process would require 2-tank days to complete the reaction, while the 2-stage would require only 1.24 tank-days to achieve the same effect. This difference represents an approximately 38% savings in tankage and a 75% savings of the enzyme usage resulting from the 2-stage process.

EXAMPLE 3

High concentration collagen solids slurries are prepared in 35-gallon drums (39 in number). Each drum contains 250 pounds total at 2.5% collagen solids at a pH adjusted to about 1.8. Pepsin is added at a rate of 0.02 g/g collagen solids with stirring to initiate the reaction. The slurries are reacted for 6 days at a temperature to a range of 14°–20° C. Thereafter, the reaction is substantially stopped for 6 days by maintaining the temperature at 5–10° C. The slurries thereafter are poured into a tank containing about 6200 gallons of tap water. The total volume is then increased to 8532 gallons with more tap water to a concentration of 0.34% collagen solids. The pH of the diluted slurry is adjusted to 2.2 with HCl. Solution temperature, pH and viscosity are measured periodically until the solution is added to the papermaking process.

Figure 3:
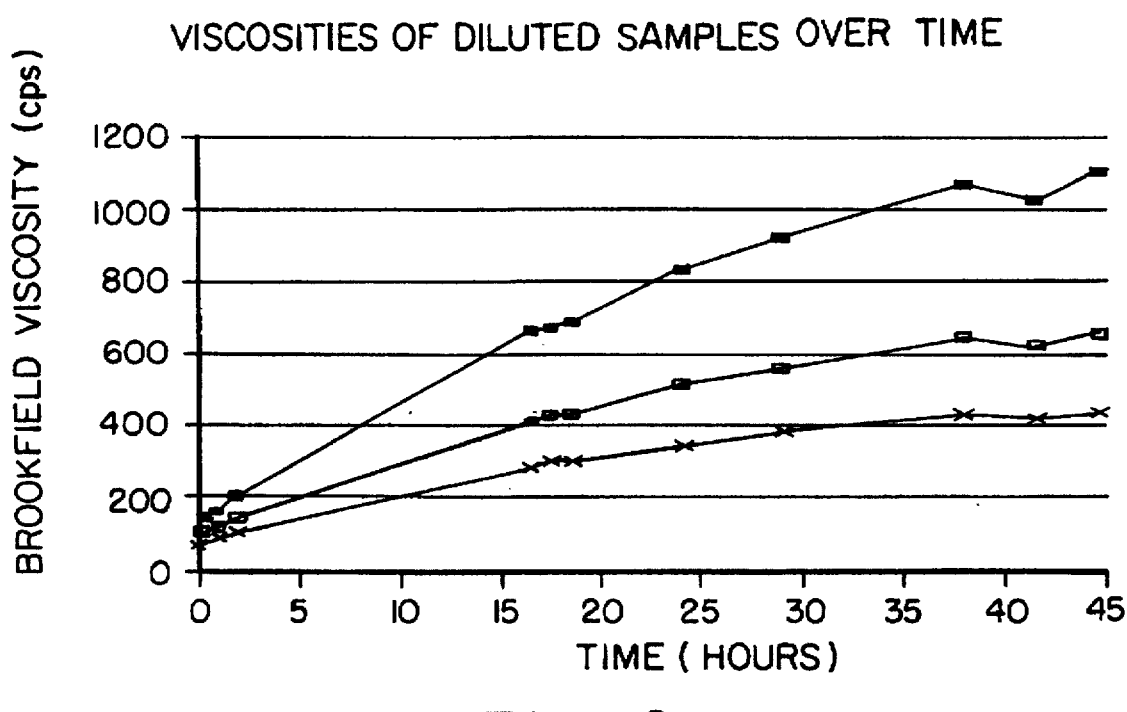
FIG. 3 is a plot of the viscosities of the diluted slurry of Example 3 over time.

The initial viscosity when the slurry is diluted is 110 cps at 12 rpm as measured on a Brookfield model LVF Viscometer. The solution appears to reach its maximum viscosity after about 40 hours. Typically, this reaction would require 2–2.5 times more enzyme to maximize the viscosity after 40 hours. The results are summarized in Table X and FIG. 3.

TABLE X

| | Viscosity at | | | |
|---|---|---|---|---|
| Time (hrs) | 12 rpm | 30 rpm | 60 rpm | Visc. Ratio |
| 0 | 110 | 85 | 63 | 1.76 |
| 0.5 | 145 | 104 | 80 | 1.82 |
| 1 | 160 | 119 | 89 | 1.80 |
| 2 | 198 | 138 | 105 | 1.89 |
| 16.5 | 663 | 403 | 282 | 2.35 |
| 17.5 | 668 | 420 | 298 | 2.24 |
| 18.5 | 688 | 432 | 302 | 2.28 |
| 24 | 833 | 512 | 344 | 2.42 |
| 29 | 918 | 559 | 378 | 2.43 |
| 38 | 1065 | 640 | 429 | 2.48 |
| 41.5 | 1025 | 615 | 412 | 2.49 |
| 44.5 | 1095 | 650 | 433 | 2.53 |

EXAMPLE 4

High concentration collagen solids slurries are prepared in 35-gallon drums from 612 lbs ground limed split bovine hides at 25% collagen solids. Each drum is filled with the ground hides and tap water to produce 5 a 3.5% collagen solids slurry. The pH is adjusted to about 2.0 with HCl. Pepsin (Sigma Lot No. 45H0867) is added to the slurry at a rate of 0.03 lb/lb collagen solids. Each drum is stirred thoroughly to initiate the reaction. The slurries react at about 20° C. for 4 days and then are stored at 5°–10° C. for 16 days. By lowering the temperature the reaction is effectively interrupted.

The reaction is resumed when the drums are poured into a tank containing enough tap water to bring the total volume to about 6168 gallons. The diluted concentration is at 0.30% collagen solids. The mixture is stirred and he pH is adjusted to about 2.2 with HCl. The average reaction temperature is 26° C.

Temperature, pH and viscosity are measured periodically during the reaction. The initial viscosity of the 0.30% mixture is 98 cps at 12 rpm as measured on a Brookfield model LVF Viscometer. The solution reached its peak viscosity after about 24 hours. The results are summarized in the following Table XI.

TABLE XI

Viscosity of Diluted Samples Over Time

| Time (hrs) | 12 rpm | 30 rpm | 60 rpm | Visc. Ratio |
|---|---|---|---|---|
| 0 | 98 | 68 | 49 | 1.99 |
| 0.5 | 98 | 68 | 49 | 1.99 |
| 1 | 105 | 75 | 55 | 1.91 |
| 2 | 138 | 98 | 76 | 1.81 |
| 3 | 163 | 118 | 90 | 1.81 |
| 19 | 688 | 439 | 308 | 2.24 |
| 20 | 710 | 450 | 314 | 2.26 |
| 21 | 720 | 458 | 317 | 2.27 |
| 28 | 743 | 472 | 324 | 2.29 |
| 41 | 715 | 453 | 315 | 2.27 |

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

We claim:

1. An improved method for producing an aqueous solution of soluble collagen comprising the steps of:

(A) providing an aqueous ground slurry of insoluble collagen containing from about 2.0% to about 5.0% by weight of insoluble collagen at a pH effective to obtain activity for a proteolytic enzyme added in step (B);

(B) adding a proteolytic enzyme to said slurry;

(C) reacting said slurry and enzyme at a temperature, $T_1$ and for a time $t_1$ effective for forming a slurry containing at least some soluble collagen;

(D) diluting at least a portion of the slurry formed in step (C) with water to form a diluted slurry containing from about 0.1% to about 1% by weight of insoluble collagen; and (E) reacting said diluted slurry obtained in step (D) at a temperature, $T_2$ and for a time $t_2$ effective to produce a solution containing an increased amount of soluble collagen.

2. The method of claim 1 wherein the aqueous ground slurry provided in (A) contains from about 2.0% to about 3.5% by weight of insoluble collagen.

3. The method of claim 1 wherein the aqueous ground slurry provided in (A) contains from about 3.0% to about 3.5% by weight of insoluble collagen.

4. The method of claim 1 wherein the slurry formed in step (D) contains from about 0.20% to about 0.40% by weight of insoluble collagen.

5. The method of claim 1 wherein temperatures $T_1$ in step (C) and $T_2$ in step (E) are each independently from about 5° C. to about 35° C.

6. The method of claim 1 wherein $t_1$ is from about 12 hours to about 20 days.

7. The method of claim 1 wherein $t_1$ is from about 12 to about 24 hours.

8. The method of claim 1 wherein the pH of the diluted slurry obtained in step (D) is adjusted to maintain activity for the proteolytic enzyme present in the diluted slurry.

9. The method of claim 8 wherein the pH is adjusted to between about 1.5 and about 3.0.

10. The method of claim 1 wherein the pH of the slurry provided in step (A) is between about 1.5 and 3.0.

11. The method of claim 1 wherein the proteolytic enzyme added in step (B) is an enzyme selected from the group consisting of porcine mucosal pepsin, bromelain, chymopapain, chymotrypsin, collagenase, ficin, papain, peptidase, proteinase A, proteinase K, trypsin, microbial proteases, and combinations of such enzymes.

12. The method of claim 1 wherein the reaction in (E) is terminated by rendering the proteolytic enzyme inactive by adjusting the pH of the diluted slurry; and/or reducing the temperature of said diluted slurry.

13. The method of claim 1 further comprising monitoring said reaction in step (E) and continuing the reaction until soluble collagen of a desired number average molecular weight is obtained.

14. The method of claim 1 further comprising monitoring said reaction in step (E) by measuring the solution viscosity of the diluted slurry at two different shear rates whereby said reaction is complete when a ratio of (viscosity at low shear)/(viscosity at high shear) is substantially maximized.

15. The method of claim 14 wherein said viscosity ratio is at least about 75% of the maximum attained.

16. The method of claim 1 further comprising monitoring said reaction in step (E) by measuring the concentration and the number average molecular weight ($\overline{Mn}$) of the soluble collagen whereby said reaction is considered complete when said concentration and said $\overline{Mn}$ are maximized.

17. The method of claim 1 wherein the soluble collagen obtained has a number average molecular weight of at least about 300,000 daltons.

18. An aqueous solution of solubilized collagen prepared in accordance with the method of claim 1.

19. An improved method for producing an aqueous solution of solubilized collagen comprising:

(A) providing an aqueous ground slurry containing from about 2.0% to about 3.5% by weight of insoluble collagen at a pH sufficient to obtain activity for a proteolytic enzyme added in step (B);

(B) adding said proteolytic enzyme to said slurry and reacting said enzyme with said insoluble collagen at a temperature $T_1$, and for a time $t_1$ to produce a slurry containing at least some soluble collagen;

(C) diluting at least a portion of the slurry obtained in (B) with water to form a diluted slurry containing the proteolytic enzyme and from about 0.1% to about 1.0% by weight of insoluble collagen;

(D) reacting said diluted slurry and enzyme at a temperature $T_2$, and for a time $t_2$, effective to produce a solution containing an increased amount of soluble collagen; and (E) withdrawing said solution of soluble collagen as product.

20. The method of claim 19 wherein the reaction in step (D) is controlled to obtain a solution having a high concentration of soluble collagen by measuring the concentration and $\overline{M}n$ of soluble collagen, whereby said reaction is considered complete when said $\overline{M}n$ is at least about 300,000 daltons and said concentration of said soluble collagen is maximized.

21. The method of claim 19 wherein the aqueous ground slurry provided in step (A) contains from about 3.0% to about 3.5% by weight of insoluble collagen.

22. The method of claim 19 wherein the pH of the aqueous ground slurry provided in step (A) is from about 1.5 to about 3.

23. The method of claim 19 wherein $t_1$ is from about 12 hours to about 20 days.

24. The method of claim 19 wherein $t_2$ is from about 6 to about 30 hours.

25. The method of claim 19 wherein the temperatures $T_1$ and $T_2$ are each independently within the range of from about 5° C. to about 35° C.

26. The method of claim 19 wherein the pH of the diluted slurry formed in step (C) is adjusted to be within the range of about 1:5 to about 3.

27. The method of claim 19 wherein the proteolytic enzyme added in step (B) is an enzyme selected from the group consisting of porcine mucosal pepsin, bromelain, chymopapain, chymotrypsin, collagenase, ficin, papain, peptidase, proteinase A, proteinase K, trypsin, microbial proteases, and combinations of such enzymes.

28. The method of claim 19 wherein the reaction in step (D) is terminated by rendering the proteolytic enzyme inactive by adjusting the pH of the diluted slurry and/or reducing the temperature of the diluted slurry.

29. An aqueous solution of solubilized collagen prepared in accordance with the method of claim 19.

* * * * *